United States Patent [19]

Batista et al.

[11] Patent Number: 5,296,233
[45] Date of Patent: Mar. 22, 1994

[54] DUAL SUBCOATED SIMULATED CAPSULE-LIKE MEDICAMENT

[75] Inventors: Marli F. Batista, Lower Gwynedd; Thomas J. Markley, Lansdale, both of Pa.

[73] Assignee: McNeil-PPC, Inc., Milltown, N.J.

[21] Appl. No.: 989,407

[22] Filed: Dec. 11, 1992

Related U.S. Application Data

[62] Division of Ser. No. 468,434, Jan. 22, 1990, Pat. No. 5,198,227.

[51] Int. Cl.$^5$ .................... A61K 9/40; A61K 9/48
[52] U.S. Cl. .................... 424/463; 424/454; 424/456; 424/474; 424/478; 424/480; 424/482
[58] Field of Search ............... 424/454, 456, 463, 464, 424/478, 479, 482

[56] References Cited

U.S. PATENT DOCUMENTS

| | | | |
|---|---|---|---|
| 599,865 | 3/1898 | Richards | 427/3 |
| 3,185,626 | 5/1965 | Baker | 424/499 |
| 3,959,540 | 5/1976 | Leiberich et al. | 424/463 |
| 4,800,087 | 1/1989 | Mehta | 424/490 |
| 4,803,079 | 2/1989 | Hsiao et al. | 424/468 |
| 4,816,259 | 3/1989 | Matthews et al. | 424/463 |
| 4,820,524 | 4/1989 | Berta et al. | 424/474 |
| 4,857,337 | 8/1989 | Miller et al. | 424/482 |
| 4,928,840 | 5/1990 | Barshay et al. | 424/451 |
| 4,951,230 | 8/1990 | Tencza et al. | 424/467 |
| 4,966,771 | 10/1990 | Berta | 424/428 |
| 5,089,270 | 2/1992 | Hampton et al. | 424/465 |
| 5,114,720 | 5/1992 | Littell et al. | 424/478 |
| 5,188,688 | 2/1993 | Boardman et al. | 424/454 |

FOREIGN PATENT DOCUMENTS

| | | | |
|---|---|---|---|
| 1217140 | 1/1987 | Canada | 167/166 |
| 1223209 | 6/1987 | Canada | 167/164 |
| 0111144 | 2/1984 | European Pat. Off. | |
| 0212746 | 7/1986 | European Pat. Off. | |
| 0274734 | 12/1987 | European Pat. Off. | |
| 0288138 | 2/1988 | European Pat. Off. | |
| 435726 | 7/1991 | European Pat. Off. | |

OTHER PUBLICATIONS

Pharmaceutical Dosage Forms: Tablets, H. A. Lieberman, L. Lachman and J. B. Schwartz, vol. 3 pp. 108–113, Second Edition (1990).

Remington's Pharmaceutical Sciences, 18th Edition, p. 1667 (1990).

*Primary Examiner*—Thurman K. Page
*Assistant Examiner*—Amy Hulina

[57] ABSTRACT

A simulated capsule-like medicament comprising a dual subcoating comprising an initial subcoating of a water soluble film forming polymer, e.g. povidone and a secondary subcoating of a mixture of two soluble film forming polymers, e.g. povidone and hydroxypropyl methylcellulose and a hydrophobic plasticizer, e.g. castor oil, which provides for a smooth uniform and substantially bubble free outer coating, e.g. gelatin, for the capsule-like medicament; and a process of making such medicaments.

17 Claims, No Drawings

DUAL SUBCOATED SIMULATED CAPSULE-LIKE MEDICAMENT

This is a division, of application Ser. No. 468,434, filed Jan. 22, 1990, now U.S. Pat. No. 5,198,227, which is hereby incorporated by reference.

FIELD OF THE INVENTION

This invention relates to subcoated simulated capsule-like medicaments. More particularly this invention relates to a solid medicament caplet core which has been subcoated with a mixture of at least one water-soluble, film-forming polymer and a hydrophobic plasticizer and coated with a smooth outer coating to provide the appearance of a capsule-like medicament and a process of making such coated medicaments.

BACKGROUND OF THE INVENTION

Filled two-piece gelatin capsules for the encapsulation of various medicinal agents have been used for administering drugs since the mid-19th century. This capsule form of medicament proved to be very popular because hard gelatin capsules are tasteless, easily administered and easily filled either at a pharmacy or pre-filled in large quantities at commercial plants. While hard shell gelatin capsules are still popular dosage forms for pharmacist dispensed medicaments, they have generally been discontinued in many over-the-counter products because of the risk of tampering with their contents.

Absent the susceptibility of the capsule form medicaments to tamperings the capsule form was extremely popular with consumers because of a number of advantages. Many consumers prefer the gelatin form of capsule because of the perceived efficacy, taste, feel and swallowability of the gelatin capsule form of medicament.

This consumer preference for gelatin capsule-like medicaments provided a challenge to the industry to produce capsule-like medicaments which are tamper-proof yet provide the consumer with the advantages of a hard shell gelatin capsule-like dosage form. Norbert I. Berta developed simulated capsule-like medicaments and a process for making such capsule-like medicaments as disclosed in his U.S. Pat. No. 4,820,524. The entire disclosure of this issued U.S. patent is hereby incorporated herein by reference. Norbert I. Berta has also developed variations of the processes for making simulated capsule-like medicaments and apparatus for producing such medicaments as disclosed in co-pending U.S. patent application Ser. Nos. 129,108 filed Dec. 4, 1987 now U.S. Pat. No. 4,921,108; 129,109 filed Dec. 4, 1987, now U.S. Pat. No. 4,867,983; 190,551 filed May 5, 1988, now U.S. Pat. No. 4,966,771; and 190,616 filed May 5, 1988. The simulated capsule-like medicaments developed by Berta were responsive to a long felt need in the industry to provide a simulated substitute for the popular dosage form of gelatin capsules. While gelatin coating of uncoated compressed medicaments such as acetaminophen is possible in accordance with the invention of Berta, it is difficult to control the quality of the surface appearance of such gelatin-coated caplets.

Beyond the development of a simulated capsule-like medicament several factors and considerations must be met to commercially produce a capsule-like dosage form which has a smooth, uniform and substantially bubble free outer coating appearance. A preferred gelatin-coated caplet is one in which two distinctly colored gelatin coating solutions are utilized to produce a bi-colored gelatin-coated caplet. The two overlapping distinctly colored gelatin coatings form a seam about the transverse axis of the medicament. The presence of this seam and the distinct bi-coloring contributes to the consumer's perception of these simulated capsule-like medicaments as equivalents to gelatin capsule dosage forms.

The gelatin coated caplet product must adequately simulate a capsule-like medicament from a consumer's sight and touch perspective and must, therefore, be absent of discoloration, pits and gouges. The presence of such physical imperfections may erode the consumer's perception as to the gelatin coated caplet's capsule-like nature and the tamper-free nature of this dosage form. Strong consumer confidence in the gelatin capsule-like nature and tamper-resistance of the simulated capsule medicament of the invention is of the utmost importance in the marketing of this dosage form and forms an object of the present invention. It is, therefore, an object of the present invention to provide a subcoating for a solid caplet medicament core which minimizes bubble formation, discoloration and other aesthetic imperfections to provide for a smooth, uniform and substantially bubble free outer coating appearance to simulated capsule-like medicaments.

SUMMARY OF THE INVENTION

The foregoing object of providing a simulated capsule-like medicament which has a smooth, uniform and substantially bubble free outer coating appearance has now been accomplished in accordance with the compositions and processes of the present invention.

In accordance with the purpose of the invention, as embodied and fully described herein, the invention comprises a simulated capsule-like medicament comprising: a solid caplet core comprising a medicament; a dual subcoating composition on the caplet core comprising an initial subcoating of a water soluble film forming polymer followed by a second subcoating comprising a mixture of at least one water-soluble, film-forming polymer and a hydrophobic plasticizer; and a smooth outer coating. Whereby, the subcoating composition promotes a smooth, uniform and substantially bubble free outer coating appearance to the capsule-like medicament.

In preferred embodiments of the invention the water-soluble, film-forming polymer in the initial subcoating is povidone and the water soluble film forming polymer of the second (outer) subcoating is hydroxypropyl methylcellulose or povidone but preferably a mixture of both. The hydrophobic plasticizer comprises castor oil, and the smooth outer coating composition is gelatin. In more preferred embodiments, the povidone of the initial subcoating comprises from about 0.025 to about 0.25%, more preferably about 0.075 to about 0.15% and most preferably about 0.1% by weight of the total weight of the subcoated caplet core. The povidone, hydroxypropyl methylcellulose and castor oil of the second subcoating comprise from about 2 to about 8%, more preferably about 4 to about 6%, and most preferably about 4% by weight of the total weight of the subcoated caplet core.

In further preferred embodiments of the invention the medicament comprises a composition selected from the group consisting of acetaminophen, ibuprofen, loperamide, naproxen, pseudoephedrine, dextromethorphan, chlorpheniramine, and mixtures thereof. More preferably the medicament is ibuprofen. In further preferred embodiments a solid caplet core of the capsule-like medicament has a slight convex bowed shape. Preferably, the bow represents an arcuate variance of about 1 to 5 degrees about a longitudinal axis of the caplet core.

As embodied and broadly described herein the invention further comprises a process for preparing a simulated capsule-like medicament comprising the steps of: granulating and compressing a mixture of a medicament and pharmaceutically acceptable excipients to form a solid caplet core; applying a subcoating composition comprising an initial (inner) subcoating of a water soluble film forming polymer followed by a second (outer) subcoating of one or more water soluble film forming polymers and a hydrophobic plasticizer to the solid caplet core; and applying a smooth outer coating to the subcoated caplet core to provide a smooth, uniform and substantially bubble free outer coating appearance to the capsule-like medicament. The preferred medicament components for the caplet core and the subcoating mixture are as described above. In preferred embodiments of the process of the invention the outer coating is gelatin and is applied at a temperature of from about 45° to 65° C., preferably at about 50° to 60° C.

DETAILED DESCRIPTION OF PREFERRED EMBODIMENTS OF THE INVENTION

Reference will now be made in detail to preferred embodiments of the invention, examples of which are illustrated in the following examples section.

To achieve the object of the invention of providing a simulated capsule-like medicament which has a smooth, uniform and substantially bubble-free outer coating appearance, a dual subcoating is applied to the solid appearance, a dual subcoating is applied to the solid caplet medicament core to provide a compatible coating surface for the gelatinous coating. The dual subcoating composition in accordance with the invention provides a surface for gelatinous coating that minimizes bubble formation, discoloration and other aesthetic imperfections.

The capsule-like medicament of the invention comprises a solid caplet core of a medicament which can be granulated and compressed into a caplet core utilizing conventional excipients and tableting aids. Any pharmaceutical active or medicament that is capable of being formed into a caplet core, may be used in accordance with the invention. Examples of suitable medicaments which may be utilized in accordance with the invention include, but are not limited to, acetaminophen, ibuprofen, loperamide, naproxen, pseudoephedrine, dextromethorphan, chlorpheniramine, and mixtures thereof. Preferably, the medicament is ibuprofen which can be in either a racemic mixture or substantially pure S-ibuprofen form (S-ibuprofen is the analgesic active component of the R and S racemic mixture of ibuprofen). These medicaments may be used alone or in combination such as in a sinus headache combination comprising for example, ibuprofen and pseudoephedrine.

U.S. patent application Ser. No. 345,599 filed Apr. 28, 1989, now continuation-in-part application Ser. No. 07/784,623, filed Oct. 31, 1991 discloses a subcoating for simulated capsule-like medicaments. The subcoating exemplified in this application is a single layer subcoating which comprises a mixture of hydroxypropyl methylcellulose and castor oil and is particularly suitable to acetaminophen caplet cores. This subcoating was found, however, to not provide optimal surface conditions for subcoating ibuprofen caplet cores which are provided with a smooth outer coating, e.g. gelatin coating. The dual subcoating of the present invention thus provides an advantageous alternative to this single layer subcoating.

The dual subcoating composition of the present invention was developed to provide multiple functions required for a suitable subcoat particularly for application to ibuprofen caplet cores. These functions and characteristics of the subcoat or pre-coat include the following: adequate film strength of the subcoating to allow the subcoated tablet to withstand mechanical transfer and maintain the integrity of the subcoat; compatibility of the subcoat material with the medicament to be coated; compatibility of the subcoat material with the smooth outer coating such that adequate pick-up of the smooth outer coating is achieved with a minimum of bubble formation on the final product; and compatibility of the subcoat material with the outer coating such that the subcoat does not adversely affect the color of the outer coating composition particularly where two distinct colors are utilized. Further, the initial (inner) subcoating improves the adhesion of the second (outer) subcoating to the caplet core. The initial subcoating provides an advantageously compatible surface for intimate contact and improved adhesion to the caplet core at the initial subcoating's inner surface and to the second subcoating at its opposite surface. The initial subcoating thus provides better adhesion between the materials comprising the caplet core and second subcoating than is possible if the core and second subcoating were in direct contact with each other.

The subcoating composition of the invention also provides advantageous processing functions. The subcoating helps eliminate dust and other degradation of the medicament caplet core. The subcoating also prevents contamination of the gelatin coating solution by the medicament present by providing a full separation barrier between the gelatin coating solution and the medicament in the subcoated solid caplet core.

In accordance with the present invention, it was found that a subcoating composition which accomplishes the required functions comprises an initial subcoating of a water soluble film forming polymer followed by a second subcoating of at least one water soluble film forming polymer and a hydrophobic plasticizer. The preferred water soluble film forming polymer for the initial subcoating is povidone (polyvinylpyrrolidone). The preferred water soluble film forming polymers for the secondary subcoating are povidone and hydroxypropyl methylcellulose, more preferably a mixture thereof and a preferred hydrophobic plasticizer is castor oil. The amount of subcoating composition utilized should be an amount effective to provide the above-mentioned desirable functions and characteristics of the subcoated caplet core.

The povidone used is preferably a mixture of a more flexible lower chain length povidone, e.g. K-25 grade, with a stronger, longer chain length povidone, e.g. K-90 grade, to provide a film of optimal flexibility and strength. For example, the ratio of K-25 to K-90 grade povidone may be from 1:1 to 1:2.5, preferably 1:2.

Optimization of the coating amount will vary in accordance with the size of the caplet core and particular medicaments utilized. Preferably, the povidone of the initial subcoating comprises about 0.025 to about 0.25%, more preferably about 0.075 to about 0.15% and most preferably about 0.1% of the total weight of the caplet core. The preferred second subcoating composition is a mixture of povidone, hydroxypropyl methylcellulose and castor oil and comprises from about 2 to about 8%, more preferably about 4 to about 6% and most preferably about 4% by weight of the total weight of the subcoated caplet core. The amount of castor oil present as a hydrophobic plasticizer comprises from about 0.1 to about 1% by weight of the total weight of the subcoated caplet core. Preferably the amount of povidone to hydroxypropyl methylcellulose is on the order of about 1:10 to about 1:15. Preferably the amount of water soluble film forming polymers, e.g. povidone and hydroxypropyl methylcellulose, to the hydrophobic plasticizer, e.g. castor oil, is on the order of about 20:1.

It is important that the outer coating of the simulated capsule-like medicament be smooth, uniform and substantially bubble free to provide the perception of a capsule-like medicament. To achieve superior simulation of gelatin capsule dosage forms it is preferred to use a dual color outer coating which meets at a distinct seam at about the middle of the coated medicament caplet. The preferred outer coating composition is gelatin whereby the subcoated caplet core is dipped into a gelatinous solution. More preferably opposite ends of a subcoated medicament caplet core are dipped into two gelatinous solutions of distinct color to produce a dual colored capsule-like medicament. The amount of gelatinous coating added to the product is dependent upon the outer appearance desired for the product. Generally, enough gelatinous coating must be added on to the caplet to provide a smooth uniform and bubble free outer coating appearance and provide a gelatinous feel to the touch and in the mouth of consumers swallowing the simulated capsule-like medicament. A preferred gelatinous coating add-on is about 6.0 to about 8.3% by weight of the total weight of the simulated capsule-like medicament.

In preferred embodiments the capsule-like medicament of the invention has a caplet core which has a slight convex bowed shape. This bowed shape serves two important functions. It was found that caplets of the prior art that were unbowed or had straight edges were more prone to stick to each other and form "twins." Formation of twins or twinning is the joining of one or more caplets together during processing along edges in contact with each other. Further, caplets with straight edges also tend to stick or twin together temporarily and cause surface imperfections, e.g. pitting.

It is, therefore, advantageous in preparing simulated capsule-like medicaments in accordance with the present invention, as well as, the handling of all tacky caplet cores to utilize caplets which have a slight bowed shape which reduces twinning of caplets due to contact during processing. The bowed shape minimizes the point of contact between caplets and thus reduces sticking or twinning of caplets to each other.

In preferred embodiments of the present invention, the bowing is a convex bow that stems from the middle of a longitudinal axis of the caplet core outwards toward the two ends. The bowed variance along the longitudinal axis of the caplet core is on the order of about 1 to 5 degrees. This arcuate variance is great enough to reduce the twinning of the caplets during processing without detracting from the capsule-like shape and appearance of the final medicament product which is important to its simulation of a gelatin capsule.

Another surprising advantage of providing caplets with a slightly convex bowed shape is that the shape provides an increase in tablet hardness of up to about 10% as compared with regular unbowed caplet shaped cores. The increase in hardness may be due to some degree to the increased thickness of the caplet about the center area, but the magnitude of increase achieved could not be anticipated by this slight change in thickness at this area. It has also been found advantageous to provide a convex bow shaped caplet, since the increased hardness contributes to preventing surface pitting and breaking of the cores during the coating process.

In accordance with the present invention, a process is also provided for preparing simulated capsule-like medicaments. The process comprises the steps of granulating and compressing a mixture of medicament and compatible excipients to form a solid caplet core. The excipients chosen and the compression applied should be adequate to provide a caplet with sufficient hardness for prevention of surface pitting and caplet breakage during coating of the caplet core. For capsule-like ibuprofen medicaments the preferred hardness is about 7-10 Kp and more preferably about 7-9 Kp.

To provide a capsule shape appearance the thickness ratio about the simulated capsule-like medicament should be as close as possible to one (1). A preferred tooling dimension for ibuprofen caplets which gives this appearance is 0.602 inches by 0.200 inches by 0.060 inches. The thickness resulting from this tooling is 0.197 inches. These dimensions may vary as the size of the caplet varies, but efforts should be made to keep the width to thickness ratios as close as possible to one (1) to provide adequate simulation of a gelatin capsule dosage form. Gelatin capsule dosage forms are generally round in shape, and therefore, have a width to thickness ratio by definition of 1.

The initial subcoating composition, preferably povidone is applied from a 5% weight by weight aqueous solution. Acceptable initial subcoating applications can be applied with solutions from 1 to 10% weight by weight, but 5% is preferred to ensure consistency of the coating. The secondary subcoating composition, preferably a mixture of povidone, hydroxypropyl methylcellulose and castor oil, is applied from an 8% weight by weight aqueous solution. Acceptable subcoatings can be applied with subcoating solutions of concentration of from 6 to 8%, but 8% is preferred since a shorter amount of spraying time is required to provide the desired amount of subcoating on the caplet core. Coating levels above 8% were found to provide less desirable subcoatings because of unevenness of application of the subcoating composition. The concentration of both the initial and the second subcoating solutions is not considered critical to the coating process. The caplet cores are subcoated to preferably provide an initial subcoating of about 0.025 to about 0.25%, more preferably about 0.075 to about 0.15% and most preferably about 0.1% by weight of the core caplet and a secondary subcoating to preferably provide about 2 to 8%, more preferably about 4 to 6% and most preferably about 4% subcoating by weight of the total weight of the subcoated caplet core.

A smooth outer coating is applied to the subcoated caplet core to provide a smooth, uniform and substantially bubble free outer coating appearance to the capsule-like medicament. The preferred outer coating is a gelatin outer coating and more preferably a bi-color gelatin coating. Application of the gelatinous coating is by dipping of the subcoated caplet core into a gelatin solution which has a temperature in the range of about 45°–65° C. The "Gelatin Solution" as used herein is meant to include suspensions of gelatin coating materials which may include coloring and opacifying agents, e.g. titanium dioxide and iron oxide. Higher gelatin solution temperatures generally result in a lower viscosity of the gelatin solution. As the gelatin solution temperature goes up and viscosity goes down, less gelatin is picked up by a subcoated caplet, because the gelatin solution is thinner and less adherent to the subcoated caplet. The relatively high temperature for the gelatin solution of 45° to 65° C. and preferably about 60° C. is advantageous because of reduction in microbial growth and contamination at these high temperatures. It is the dual subcoating of the invention which provides an improved adhesion surface for the gelatin that permits the solution to be applied at higher temperatures and lower viscosity.

Gelatin dipping may be performed by any adequate means including hand dipping of the caplets into a gelatin solution. A particularly preferred method is performed in accordance with the teachings of Berta in the aforementioned U.S. Pat. Nos. 4,820,524 which has been incorporated herein by reference. This patent provides a useful process for providing bi-color gelatin coated capsule-like medicaments which have a slightly raised seam about the color overlapping portion of the caplet which contributes to its simulated capsule-like feel and appearance. Any color gelatin solutions may be utilized, but it is preferred that the colors be distinct.

EXAMPLE

The invention will now be illustrated by example. The example is not intended to be limiting of the scope of the present invention but read in conjunction with the detailed and general description above provides further understanding of the present invention and an outline of a process for preparing the compositions of the invention.

EXAMPLE 1

Simulated Capsule-like Ibuprofen Dosage Form

An ibuprofen capsule-like gelatin coated dosage form ("gelcap") is prepared from the following ingredients.

| Ingredients: | mg/Caplet* |
|---|---|
| A. Ibuprofen Granulation | |
| Ibuprofen USP | 200.00 |
| Microcrystalline Cellulose NF | 40.00 |
| Starch NF (Corn) | 40.00 |
| Pregelatinized Starch NF | 20.00 |
| Sodium Starch Glycolate NF | 8.00 |
| Hydroxypropyl Methylcellulose USP | 2.00 |
| Purified Water** | 9.50 |
| B. Dry Additives: | |
| Sodium Starch Glycolate NF | 2.00 |
| Colloidal Silicon Dioxide NF | 1.00 |
| C. Film Coat: | |
| Povidone USP (K-25) | 0.437 |
| Povidone USP (K-90) | 0.875 |
| A 20:1 Mixture of Hydroxypropyl methylcellulose and castor oil | 12.00 |
| Purified Water USP** | 9.50 |
| D. Gelatin Coat: | |
| Opaque Grey Gelatin | 15.00 |

| -continued | |
|---|---|
| Ingredients: | mg/Caplet* |
| Opaque Red Gelatin | 13.00 |
| Total Weight of Gelcap | 354.312 |

*Variation in quantity of all excipients may be ±10%.
**Purified Water is used to produce the granulation and coat the caplets and is removed on drying.

Working Directions

1. Pass the ibuprofen through a mechanical impact mill (e.g., Entoleter), if necessary, to reduce agglomerates.
2. Place the ibuprofen, microcrystalline cellulose, starch, pregelatinized starch and sodium starch glycolate into a high intensity mixer/granulator (e.g., Fielder) and blend. Add hydroxypropyl methylcellulose as a 0.5% to 5.0% aqueous solution while mixing to granulate. Use additional purified water as needed to achieve a suitable granulation.
3. Pass the wet granulation, if needed to reduce agglomerates, through a mill (e.g., Comil) or a centrifugal sifting machine (e.g., Glatt Quick Sieve).
4. Dry the granulation in a fluid bed dryer (e.g., Aeromatic, Glatt).
5. Add the dry additives (sodium starch glycolate and colloidal silicon dioxide) to the dried ibuprofen granulation.
6. Pass the dried granulation with dry additive through a stainless steel screen on a centrifugal sifting machine (e.g., Glatt Quick Sieve).
7. Blend the milled ibuprofen granulation with dry additives in a stainless steel blender (e.g, Patterson Kelly twin shell blender, Tote Bin blender). 8. Compress on a rotary tablet press (e.g., Manesty, Fette) at the indicated weight, using the prescribed punches and dies.
9. Aqueous film coat the caplets with an aqueous solution of Povidone K-25 and Povidone K-90 followed by an aqueous solution of Povidone K-25, Povidone K-90 and a 20:1 mixture of hydroxypropyl methylcellulose and castor oil using a side vented coating pan (e.g., Accela Cota, Vector).
10. Discharge the coated caplets from the coating pan.

Gelatin Dipping

The subcoated caplet core is then subjected to gelatin dipping which may be accomplished by hand, e.g. by dipping half of the subcoated caplet core into an opaque grey gelation solution at about 60° C. for about 6 seconds and withdrawing the half coated caplet and allowing it to dry before dipping the as yet non-gelatin coated half of the caplet into an opaque red gelatin solution at a temperature of 60° C. for about 6 seconds. Whereby a slight overlapping of the two distinctly colored gelatinous cores is achieved about the midway portion of the caplet.

The caplet may also be gel dipped in-accordance with the process and apparatus as described in U.S. Pat. No. 4,820,524 of Berta which has been incorporated herein by reference. For example, using a modified hard gelatin capsule forming machine, dip slightly more than half the coated caplet in Opaque Grey gelatin, and allow the gelatin to dry. Grip the gelatin coated half of the caplet and dip approximately half the caplet in Opaque Red gelatin and allow to dry.

The scope of the present invention is not limited by the description, examples and suggested uses herein and modifications can be made without departing from the spirit of the invention. For example, other components may be added to the caplet core including various flavorings, preservatives and other pharmaceutical excipients. The present invention may also be provided in a sustained release formulation wherein the caplet core comprises a medicament and sustained release promoting excipients. The simulated capsule-like compositions and slightly bowed caplets may also be applicable to non-medicinal applications such as oral dosage forms of vitamins and/or other nutrients.

Application of the compositions and processes of the present invention for medical and pharmaceutical uses can be accomplished by clinical, medical and pharmaceutical methods and techniques as are presently or prospectively known to those skilled in the art. Thus it is intended that the present invention cover the modifications and variations of this invention provided that they come within the scope of the appended claims and their equivalents.

What is claimed:

1. A simulated capsule medicament comprising: a solid caplet core comprising a medicament; a dual subcoating composition on the caplet core comprising an initial subcoating applied to the caplet core comprising povidone and a second subcoating comprising a mixture of povidone, hydroxypropyl comprising and castor oil; and a smooth gelatinous outer coating.

2. The capsule medicament of claim 1 wherein the initial subcoating composition comprises about 0.025 to about 0.25% by weight of the dual subcoated caplet core and the second subcoating composition comprises from about 2 to about 8% by weight of the total weight of the dual subcoated caplet core.

3. The capsule medicament of claim 1 wherein the initial subcoating composition comprises about 0.075 to about 0.15% by weight of the subcoated caplet core and the second subcoating composition comprises from about 4 to about 6% by weight of the total weight of the dual subcoated caplet core.

4. The capsule medicament of claim 1 wherein the initial subcoating composition comprises about 0.1% and the second subcoating composition about 4% by weight of the dual subcoated caplet core.

5. The capsule medicament according to claim 1 wherein the castor oil comprises from about 0.1 to about 1.0% by weight of the total weight of the subcoated caplet core.

6. The capsule medicament of claim 2 wherein the ratio of povidone to hydroxypropyl methylcellulose in the second subcoating is in the range of about 1:10 to about 1:15 and the ratio of hydroxypropyl methylcellulose to castor oil is about 20:1.

7. The capsule medicament according to claim 3 wherein the medicament comprises a combination of ibuprofen and pseudoephedrine.

8. The capsule medicament according to claim 1 wherein the medicament is ibuprofen.

9. The capsule medicament according to claim 1 wherein the medicament is naproxen.

10. The capsule medicament according to claim 1 wherein the medicament is loperamide.

11. The capsule medicament according to claim 1 wherein the medicament comprises a combination of ibuprofen and pseudoephedrine.

12. A simulated capsule medicament comprising: a solid caplet medicament core having a slight convex bowed shape; a dual subcoating composition on the caplet core comprising an initial subcoating comprising about 0.1% povidone and a second subcoating comprising about 4% of a mixture of hydroxypropyl methylcellulose and castor oil by weight of the total weight of the subcoated caplet core; and a smooth gelatinous outer coating.

13. The capsule medicament according to claim 12 wherein the medicament is selected from the group consisting of acetaminophen, ibuprofen, loperamide, naproxen, pseudoephedrine, dextromethorphan, chlorphenarimine, and mixtures thereof.

14. The capsule medicament according to claim 12 wherein the medicament is ibuprofen.

15. A simulated capsule medicament, comprising:
    a solid caplet core comprising a medicament;
    a dual subcoating composition on the caplet core comprising an initial subcoating applied to the caplet core comprising povidone and a second subcoating comprising a mixture of (a) a polymer selected from the group consisting of povidone, hydroxypropyl methylcellulose, and mixtures thereof and (b) castor oil; and
    a smooth gelatinous outer coating.

16. The capsule medicament of claim 1 wherein the initial subcoating composition comprises about 0.025 to about 0.25% by weight of the dual subcoated caplet core and the second subcoating composition comprises from about 2 to about 8% by weight of the total weight of the dual subcoated caplet core.

17. The capsule medicament of claim 1 wherein the medicament is selected from the group consisting of acetaminophen, ibuprofen, loperamide, naproxen, pseudoephedrine, dextromethorphan, chlorphenarimine, and mixture thereof.

* * * * *